(12) United States Patent
Mower et al.

(10) Patent No.: US 9,610,446 B2
(45) Date of Patent: *Apr. 4, 2017

(54) SYSTEM AND METHOD FOR STIMULATING THE HEART USING SUB-THRESHOLD BIPHASIC STIMULATION

(71) Applicant: MR3 MEDICAL, LLC, North Oaks, MN (US)

(72) Inventors: Morton M. Mower, Denver, CO (US); Ralph Hall, North Oaks, MN (US)

(73) Assignee: MR3 MEDICAL, LLC, North Oaks, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,039

(22) Filed: Feb. 8, 2016

(65) Prior Publication Data
US 2016/0151627 A1 Jun. 2, 2016

Related U.S. Application Data

(63) Continuation of application No. 14/284,197, filed on May 21, 2014.

(60) Provisional application No. 61/825,708, filed on May 21, 2013.

(51) Int. Cl.
*A61N 1/362* (2006.01)
*A61N 1/368* (2006.01)

(52) U.S. Cl.
CPC .......... *A61N 1/368* (2013.01); *A61N 1/3628* (2013.01)

(58) Field of Classification Search
CPC .................................................. A61N 1/3628
See application file for complete search history.

(56) References Cited

U.S. PATENT DOCUMENTS

| 6,233,484 B1 | 5/2001 | Ben-Haim et al. |
| 6,629,931 B1* | 10/2003 | Begemann ........... A61N 1/3702 |
| | | 600/508 |
| 7,751,888 B1* | 7/2010 | Schecter .............. A61N 1/3627 |
| | | 607/17 |
| 2002/0052632 A1* | 5/2002 | Ben-Haim ........... A61B 5/0215 |
| | | 607/9 |
| 2004/0215254 A1 | 10/2004 | Boute |
| 2008/0280341 A1* | 11/2008 | KenKnight ............ A61N 1/362 |
| | | 435/173.6 |
| 2010/0069985 A1* | 3/2010 | Stahmann .......... A61N 1/36185 |
| | | 607/9 |

(Continued)

OTHER PUBLICATIONS

Stefano Pietronave, et al. "Monophasic and Biphasic Electrical Stimulation Induces a Precardiac Differentiation in Progenitor Cells Isolated from Human Heart" Stem Cells and Development, vol. 23, No. 8, 2014, 12 pages, from Italy.

(Continued)

*Primary Examiner* — Eugene T Wu
(74) *Attorney, Agent, or Firm* — Oblon, McClelland, Maier & Neustadt, L.L.P.

(57) ABSTRACT

A rules engine acquires sensor data from sensors applied to the heart and determines whether an electrical waveform should be applied to the heart and, if so, the type of electrical waveform. A multiphase cardiac stimulus generator generates waveforms in response to the rules engine. The electrical waveform is applied to one or more electrodes implanted in or on the heart.

12 Claims, 2 Drawing Sheets

(56) References Cited

U.S. PATENT DOCUMENTS

| | | | |
|---|---|---|---|
| 2013/0006318 A1* | 1/2013 | Weiss | A61N 1/36521 |
| | | | 607/4 |
| 2014/0350624 A1 | 11/2014 | Mower | |
| 2014/0350625 A1 | 11/2014 | Mower | |
| 2014/0350626 A1 | 11/2014 | Mower | |
| 2014/0350627 A1 | 11/2014 | Mower | |
| 2014/0350628 A1 | 11/2014 | Mower | |
| 2015/0360025 A1 | 12/2015 | Mower | |

OTHER PUBLICATIONS

Loraine L. Y. Chiu, et al. "Biphasic Electrical Field Stimulation Aids in Tissue Engineering of Multicell-Type Cardiac Organoids" Tissue Engineering: Part A, vol. 17, Nos. 11 and 12, 2011, pp. 1465-1477, from Toronto.

* cited by examiner

SYSTEM AND METHOD FOR STIMULATING THE HEART USING SUB-THRESHOLD BIPHASIC STIMULATION

RELATED APPLICATIONS

This application is a continuation of U.S. application Ser. No. 14/284,197, entitled "System and Method for Stimulating the Heart Using Sub-threshold Biphasic Stimulation" and filed May 21, 2014, which claims the benefit of priority to U.S. Provisional Patent Application No. 61/825,708, entitled "System and Method for Stimulating the Heart Using Subthreshold Biphasic Stimulation" and filed May 21, 2013. The entire contents of both of which are hereby incorporated by reference for all purposes.

BACKGROUND

The heart is divided into the right, side and the left side. The right side, comprising the right atrium and ventricle, collects and pumps de-oxygenated blood to the lungs to pick up oxygen. The left side, comprising the left atrium and ventricle, collects and pumps oxygenated blood to the body. Oxygen-poor blood returning from the body enters the right atrium through the vena cava. The right atrium contracts, pushing blood through the tricuspid valve and into the right ventricle. The right ventricle contracts to pump blood through the pulmonic valve and into the pulmonary artery, which connects to the lungs. The blood picks up oxygen in the lungs and then travels back to the heart through the pulmonary veins. The pulmonary veins empty into the left atrium, which contracts to push oxygenated blood into the left ventricle. The left ventricle contracts, pushing the blood through the aortic valve and into the aorta, which connects to the rest of the body. Coronary arteries extending from the aorta provide the heart blood.

The heart's own pacemaker is located in the atrium and is responsible for initiation of the heartbeat. The heartbeat begins with activation of atrial tissue in the pacemaker region (i.e., the sinoatrial (SA) node), followed by cell-to-cell spread of excitation throughout the atrium. The only normal link of excitable tissue connecting the atria to the ventricles is the atrioventricular (AV) node located at the boundary between the atria and the ventricles. Propagation takes place at a slow velocity, but at the ventricular end the bundle of His (i.e., the electrical conduction pathway located in the ventricular septum) and the bundle braides carry the excitation to many sites in the right and left ventricle at a relatively high velocity of 1-2 m/s. The slow conduction in the AV junction results in a delay of around 0.1 seconds between atrial and ventricular excitation. This timing facilitates terminal filling of the ventricles from atrial contraction prior to ventricular contraction. After the slowing of the AV node, the bundle of His separates into two bundle branches (left and right) propagating along each side of the septum. The bundles ramify into Purkinje fibers that diverge to the inner sides of the ventricular walls. This insures the propagation of excitatory pulses within the ventricular conduction system proceeds at a relative high speed when compared to the propagation through the AV node.

When the heart is working properly, both of its lower chambers (ventricles) pump at the same time, synchronized with the pumping of the two upper chambers (atria). Up to 40 percent of heart failure patients, however, have disturbances in the conduction of electrical impulses to the ventricles (e.g., bundle branch block or intraventricular conduction delay). As a result, the left and right ventricles are activated at different times. When this happens, the walls of the left ventricle (the chamber responsible for pumping blood throughout the body) do not contract simultaneously, reducing the heart's efficiency as a pump. The heart typically responds by beating faster and dilating. This results in a vicious cycle of further dilation, constriction of the vessels in the body, salt and water retention, and further worsening of heart failure. These conduction delays do not respond to antiarrhythmics or other drugs.

Patients who have heart failure may be candidates to receive a pacemaker. A pacemaker is an artificial device to electrically assist in pacing the heart so that the heart may pump blood more effectively. Implantable electronic devices have been developed to treat both abnormally slow heart rates (bradycardias) and excessively rapid heart rates (tachycardias). The job of the pacemaker is to maintain a safe heart rate by delivering to the pumping chambers appropriately timed electrical impulses that replace the heart's normal rhythmic pulses. The device designed to perform this life-sustaining role consists of a power source the size of a silver dollar (containing the battery), and control circuits, wires or "leads" that connect the power source to the chambers of the heart. The leads are typically placed in contact with the right atrium or the right ventricle, or both. They allow the pacemaker to sense and stimulate in various combinations, depending on where the pacing is required.

Either cathodal or anodal current may be used to stimulate the myocardium. The pulses produced by most pacemakers are typically cathodal and excitatory. That is, the cathodal pulse is of sufficient magnitude and length to cause the heart to beat. Cathodal current comprises electrical pulses of negative polarity. This type of current depolarizes the cell membrane by discharging the membrane capacitor, and directly reduces the membrane potential toward threshold level. Cathodal current, by directly reducing the resting membrane potential toward threshold has a one-half to one-third lower threshold current in late diastole than does anodal current.

Anodal current comprises electrical pulses of positive polarity. The effect of anodal current is to hyperpolarize the resting membrane. On sudden termination of the anodal pulse, the membrane potential returns towards resting level, overshoots to threshold, and a propagated response occurs. The use of anodal current to stimulate the myocardium is generally discouraged due to the higher stimulation threshold, which leads to use of a higher current, resulting in a drain on the battery of an implanted device and impaired longevity. Additionally, the use of anodal current for cardiac stimulation was discouraged due to the suspicion that the anodal contribution to depolarization can, particularly at higher voltages, contribute to arrhythmogenesis.

It has been shown that pacing in which a combination of cathodal and anodal pulses of either a stimulating or conditioning nature preserves the improved conduction and contractility of anodal pacing while eliminating the drawback of increased stimulation threshold. The result is a depolarization wave of increased speed. This increased propagation speed results in superior cardiac contraction leading to an improvement in blood flow. Improved stimulation at a lower voltage level also results in reduction in power consumption and increased life for pacemaker batteries.

SUMMARY

In an embodiment, sensors are applied to the heart. If the sensors indicate that the heart rate is normal, and the chambers are still functioning but contractions appear to be weakening, a sub-threshold biphasic waveform can be given to either the atria or the ventricles. On sensing the depolarization of either the atrium or ventricles, the biphasic waveform can be stopped. In the case of giving the treatment to the ventricles, they will directly be strengthened by the anodal pre-conditioning. In the case of the atrial reduction of strength of contractions, the impulse given directly to the atrium will strengthen the function of that chamber.

Because there are multiple feedback mechanisms in the heart, when weak atrial contractions lead to inadequate filling of the ventricles and poor loading of the left ventricle prior to systole, this can be reversed by biphasic treatment to the atria providing an adequate amount of blood to the ventricle and aiding both chambers.

When this is sensed not to be giving adequate treatment, a biphasic waveform can additionally be given to the ventricle as well. After any cycle where the atrium or ventricles do not depolarize on their own, the biphasic waveform is stopped after a reasonable time, generally on the order of the QT interval, which is approximately 400 milliseconds (ms). For the next heartbeat, the amplitude of the cathodal pan of the biphasic waveform can be increased, and this can occur repeatedly time after time until the contraction does occur.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

As used herein, the term "pulse" refers to a single occurrence of an electrical signal that has a defined shaped and period.

As used herein, the term "waveform" refers to a repeating electrical signal that may include one or more pulses. The pulses that make up the waveform may be the same or may differ in any one of shape, polarity, duration and amplitude. For example, a biphasic waveform may include an anodal pulse and a cathodal pulse. The anodal and cathodal components may differ only in polarity or may be differ in shape, polarity, duration and amplitude. Pulses making up a waveform may differ in shape, polarity, duration, and amplitude but be equivalent in power.

As used herein, the term "sub-threshold waveform" refers to a waveform that does not result in stimulating the heart to beat. A waveform may be sub-threshold because the amplitude of the waveform is below an amplitude threshold value necessary to stimulate a heartbeat. A waveform may be sub-threshold because the duration of the waveform is below a duration threshold value necessary to stimulate a heartbeat. A waveform may be sub-threshold because the power of the waveform is below a power threshold value necessary to stimulate a heartbeat.

As used herein, the term "pacing waveform" refers to a waveform that stimulates a heartbeat, results in depolarization and is by definition equal to or greater than a threshold necessary to simulate a heartbeat.

Figure 1:
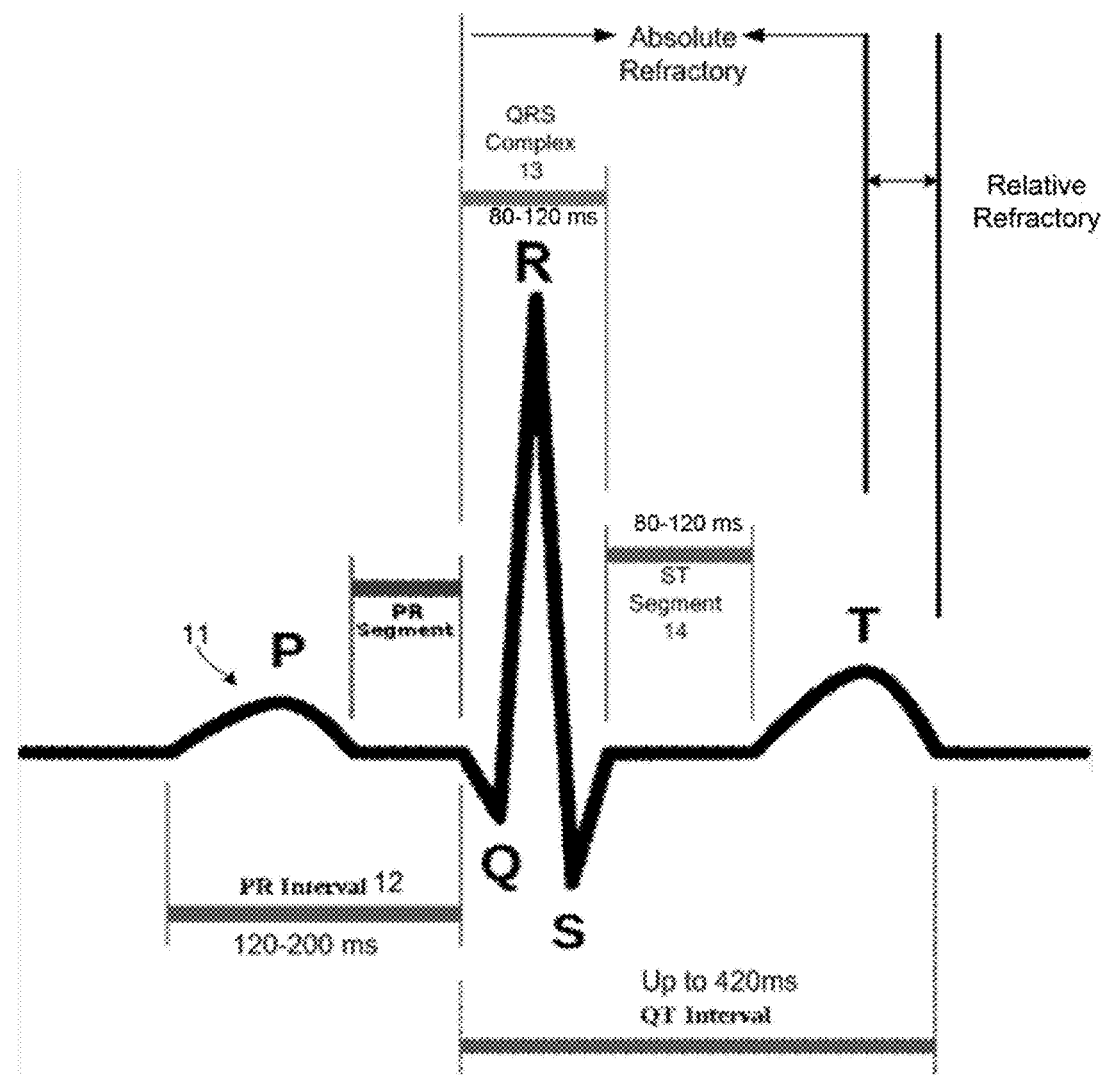
FIG. 1 is a schematic representation of the electrical activity of a typical heart beat as is known in the prior art.

FIG. 1 shows a representative tracing 10 of electrical activity in a typical heartbeat. A P wave 11 represents the wave of depolarization that spreads from the SA node throughout the atria. A period of time from the onset of the P wave to the beginning of a QRS complex is known as the P-R interval 12. The PR interval 12 represents the time between the onset of atrial depolarization and the onset of ventricular depolarization (typically lasting 20-200 ms). If the P-R interval is >200 ms, there is an AV conduction block, which is also known as a first-degree heart block if the impulse is still able to be conducted into the ventricles.

A QRS complex 13 represents the period of ventricular depolarization, which normally occurs very rapidly (e.g., typically lasting 80-120 ms). If the QRS complex is prolonged, conduction is impaired within the ventricles.

The isoelectric period (ST segment 14) following the QRS complex 13 is the period of time (typically lasting 80-120 ms) at which the entire ventricle is depolarized and roughly corresponds to the plateau phase of the ventricular action potential. The ST segment 14 is important in the diagnosis of ventricular ischemia or hypoxia because under those conditions, the ST segment 14 can become either depressed or elevated.

Figure 2:
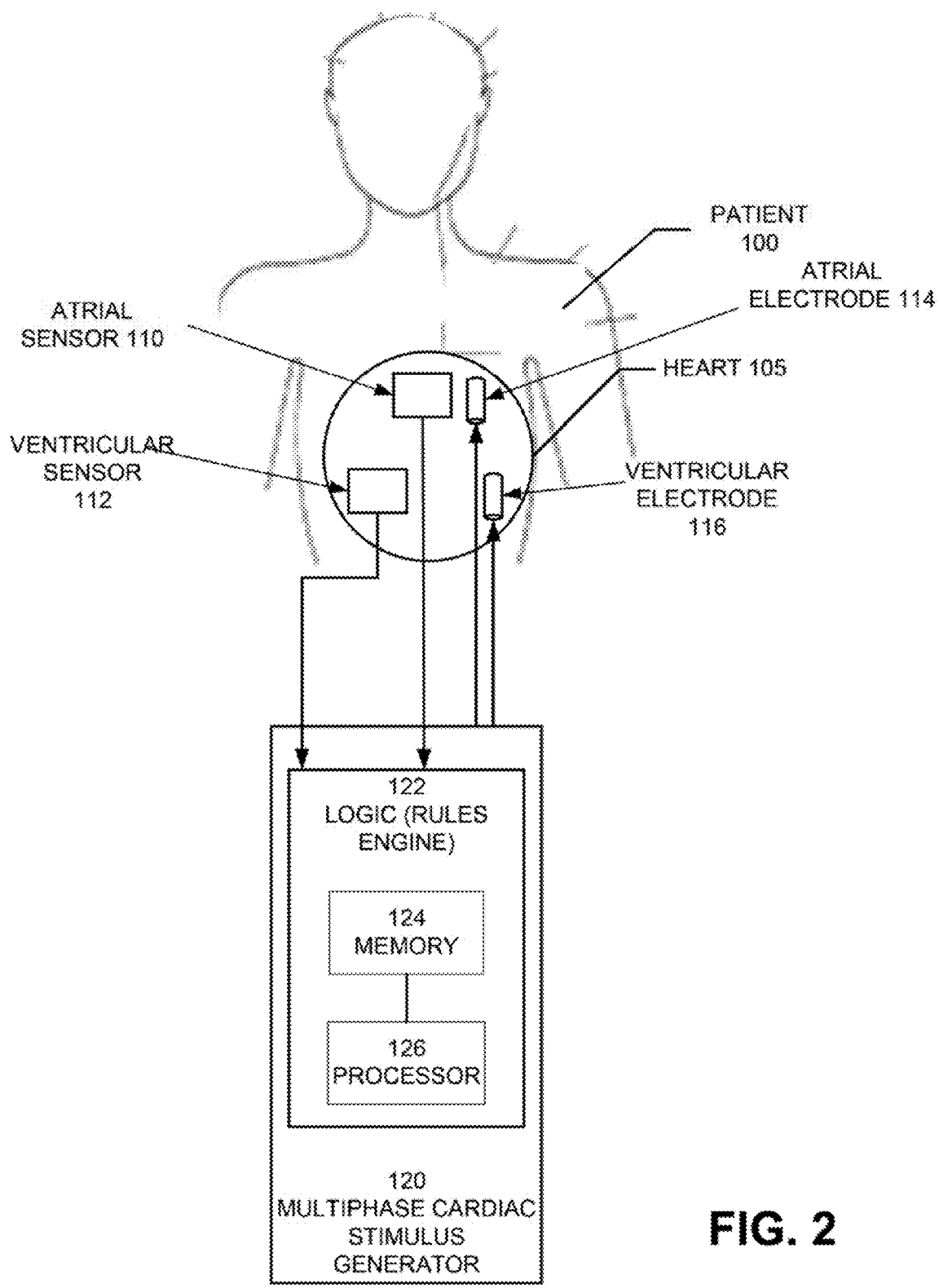
FIG. 2 is a schematic representation illustrating a cardiac stimulation device according to an embodiment.

FIG. 2 is a schematic representation illustrating a multiphase cardiac stimulus generator 120 implanted in a patient according to an embodiment. In an embodiment, one or more sensors sense rhythm and contractions of the patient's heart 105 using at least one of atrial sensing and ventricular sensing, such as at least one of atrial sensor 110 and ventricular sensor 112. The atrial sensor 110 and/or ventricular sensor 112 provide sensor data to a rules engine 122. In an embodiment, the rules engine includes a processor 126 and a memory 124 for storing rules and receiving sensor data. The rules engine 122 may poll the one or more of the atrial sensor 110 and the ventricular sensor 112 to obtain sensor data and to apply the rules to the sensor data to determine whether to deliver electrical waveforms to one or more electrodes, and, if electrical waveforms are to be delivered, which of the one or more electrodes is to receive the electrical waveforms. In an embodiment, the one or more electrodes may be an atrial electrode 114 and a ventricular electrode 116, and may provide electrical waveforms to at least one of an atrial chamber and a ventricular chamber of the heart 105. The multiphase cardiac stimulus generator 120 may generate an anodal waveform, a cathodal waveform, and a biphasic waveform above or below threshold depending on the sensor data and the rules applied by the rules engine 122.

In embodiment, if the sensor data indicate that the heart rate is normal, and the chambers are still functioning but that the contractions of the heart are weakening, the multiphase cardiac stimulus generator 120 generates a sub-threshold biphasic waveform. The sub-threshold biphasic waveform may be applied to either the atria or the ventricles. For example, the sub-threshold biphasic waveform may be applied to the atrial electrode 114 or to ventricular electrode 116. In an embodiment, a PR-interval is sensed using atrial sensor 110 indicating that the atrium has contracted. The sub-threshold biphasic waveform may be applied during this interval.

In an embodiment, following the administration of the sub-threshold biphasic waveform, the rules engine 122 updates the sensor data and determines whether the cardiac contractions have improved. If the contractions have improved application of sub-threshold biphasic waveforms is suspended. The rules engine 122 continues to monitor the sensor data from atrial sensor 110 to determine whether to resume the application of sub-threshold biphasic waveforms to the heart 105.

In an embodiment, following the administration of the sub-threshold biphasic waveform, the rules engine 122 used the sensor data to determine whether either the atrium or ventricles have depolarized. If depolarization is sensed, the biphasic waveform can be stopped.

The application of a sub-threshold biphasic waveform to either the ventricles or to atrium results in improved function (contraction) of the chamber to which it is applied.

In an embodiment, when weak atrial contractions lead to inadequate filling of the ventricles and poor loading of the left ventricle prior to systole, application of a sub-threshold biphasic waveform to the atria results in an increased amount of blood being supplied to the ventricle and aiding both chambers. In an embodiment, when it is sensed that application of the sub-threshold biphasic waveform alone is not providing adequate treatment, a biphasic waveform can additionally be given to the ventricle as well.

In an embodiment, in a cycle in which the atrium or ventricles do not depolarize on their own, the sub-threshold biphasic waveform is stopped after a reasonable time, generally approximately the QT interval, which is around 400 ms. For the next heart beat, the amplitude of the cathodal part of the sub-threshold biphasic waveform can be increased, and this can occur repeatedly until a contraction does occur.

In an embodiment, the rules engine 122 can determine from the sensor data received from the atrial sensor 110 whether to apply a sub-threshold biphasic waveform or a stimulatory biphasic waveform to the atrial electrode 114.

In another embodiment, a sub-threshold biphasic waveform may be administered to the atrial electrode 114 when the sensor data from the atrial sensor 110 indicate the presence of atrial fibrillation. Following application of the sub-threshold biphasic waveform to the atrial electrode 114, the rules engine 122 may monitor the one or more ventricular sensor 112 to determine whether the ventricle contracts (ventricular beat) in response to the sub-threshold biphasic waveform applied to the atrial electrode 114. In an embodiment, the ventricular beat is determined by the presence of a QRS waveform.

In another embodiment, the rules engine 122 determines whether following the application of the sub-threshold biphasic waveform to the atrial electrode 114 the heart 105 produces a QRS waveform (See, FIG. 1). When a QRS waveform is detected, the application of the sub-threshold biphasic waveform is suspended. When a QRS waveform is not detected after application of the sub-threshold biphasic waveform, the rules engine 122 causes the multiphase cardiac stimulus generator 120 to generate a cathodal pacing waveform for delivery to ventricular electrode 116. In an embodiment, the amplitude and/or the length of the cathodal waveform may be lower following the application of a sub-threshold anodal waveform to the atrial electrode 114.

A system and method for stimulating the heart using sub-threshold biphasic stimulation in an artificially paced heart have been disclosed. It will also be understood that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. An apparatus for stimulating a patient's heart, comprising:
   a multiphase cardiac stimulus generator;
   one or more sensors configured to sense parameters of a human heart;
   one or more electrodes configured to be implanted on, in, or proximate to at least one of an atrial chamber and a ventricular chamber of the heart; and
   a rules engine, including a processor and a memory configured to store rules and receive data from the one or more sensors,
   wherein the processor is configured to:
   poll the one or more sensors to obtain sensor data regarding the parameters of the human heart;
   apply the rules to the sensor data to determine whether to deliver a sub-threshold electrical waveform to at least one of the one or more electrodes;
   instruct the multiphase cardiac stimulus generator to generate the sub-threshold electrical waveform when delivery of the electrical waveform to at least one of the one or more electrodes is determined;
   deliver the sub-threshold electrical waveform at a timing determined from the sensor data; and
   update the sensor data,
   wherein the sub-threshold electrical waveform is a biphasic waveform, and
   the processor is further configured to increase a level of a cathodal part of the sub-threshold electrical waveform for a next heartbeat when the updated sensor data indicates no depolarization of the human heart within a heartbeat cycle and delivery of the sub-threshold electrical waveform is to be continued.

2. The apparatus of claim 1, wherein the processor is further configured to:
   determine whether to continue delivery of the sub-threshold electrical waveform based on the updated sensor data.

3. The apparatus of claim 2, wherein the processor is further configured to suspend delivery of the sub-threshold electrical waveform when the updated sensor data indicates that at least one chamber of the human heart has depolarized.

4. The apparatus of claim 3, wherein the processor is further configured to suspend delivery of the sub-threshold electrical waveform after a predetermined time interval when the updated sensor data indicates that the at least one chamber has not depolarized.

5. The apparatus of claim 4, wherein the predetermined time interval is substantially 400 ms.

6. The apparatus of claim 4, wherein the at least one chamber of the heart is an atrium, and the predetermined time interval corresponds to a QT interval of electrical activity of a contraction of the human heart.

7. The apparatus of claim 4, wherein the processor is further configured to cause the multiphase cardiac stimulus generator to generate a pacing waveform and to apply the pacing waveform when the updated data indicates that the at least one chamber of the heart has not depolarized.

8. The apparatus of claim 2, wherein the processor is further configured to suspend delivery of the sub-threshold electrical waveform when the updated sensor data indicates that contraction of the human heart has improved.

9. The apparatus of claim 1, wherein the processor is further configured to apply the sub-threshold electrical waveform when the sensor data indicates that the human heart is undergoing atrial fibrillation.

10. The apparatus of claim 1, wherein the sub-threshold electrical waveform is applied to at least one of the atrial chamber and the ventricular chamber.

11. An apparatus for stimulating a patient's heart, comprising:
- a multiphase cardiac stimulus generator;
- one or more sensors configured to sense parameters of a human heart;
- one or more electrodes configured to be implanted on, in, or proximate to at least one of an atrial chamber and a ventricular chamber of the heart; and
- a rules engine, including a processor and a memory configured to store rules and receive data from the one or more sensors,
- wherein the processor is configured to:
- poll the one or more sensors to obtain sensor data regarding the parameters of the human heart;
- apply the rules to the sensor data to determine whether to deliver a sub-threshold electrical waveform to at least one of the one or more electrodes;
- instruct the multiphase cardiac stimulus generator to generate the sub-threshold electrical waveform when delivery of the electrical waveform to at least one of the one or more electrodes is determined; and
- deliver the sub-threshold electrical waveform at a timing determined from the sensor data,
- wherein the sub-threshold electrical waveform is a biphasic waveform,
- wherein the processor is further configured to update the sensor data and determine whether to continue delivery of the sub-threshold electrical waveform based on the updated sensor data,
- wherein the processor is further configured to suspend delivery of the sub-threshold electrical waveform after a predetermined time interval when the updated sensor data indicates that the at least one chamber has not depolarized,
- wherein the processor is further configured to cause the multiphase cardiac stimulus generator to generate a pacing waveform and to apply the pacing waveform when the updated data indicates that the at least one chamber of the heart has not depolarized, and
- wherein the processor is further configured to increase a level of a cathodal part of the sub-threshold electrical waveform for a next heartbeat when the updated sensor data indicates no depolarization within a heartbeat cycle and delivery of the sub-threshold electrical waveform is to be continued.

12. The apparatus of claim 11, wherein the processor is further configured to increase a level of the cathodal part of the sub-threshold electrical waveform progressively for every subsequent heartbeat until depolarization of the at least one chamber of the human heart occurs.

* * * * *